US010753902B2

(12) United States Patent
Hekmatshoartabari (10) Patent No.: US 10,753,902 B2
(45) Date of Patent: Aug. 25, 2020

(54) CHIPLESS AND WIRELESS SENSOR CIRCUIT AND SENSOR TAG

(71) Applicant: International Business Machines Corporation, Armonk, NY (US)

(72) Inventor: Bahman Hekmatshoartabari, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/148,590

(22) Filed: Oct. 1, 2018

(65) Prior Publication Data

US 2020/0103371 A1    Apr. 2, 2020

(51) Int. Cl.

| G01N 27/414 | (2006.01) |
| H03K 19/0185 | (2006.01) |
| H04W 4/80 | (2018.01) |
| G06K 7/10 | (2006.01) |
| G06K 19/077 | (2006.01) |
| G08C 17/02 | (2006.01) |
| A61B 5/1468 | (2006.01) |

(52) U.S. Cl.
CPC ..... G01N 27/4148 (2013.01); G06K 7/10376 (2013.01); G06K 19/07749 (2013.01); G08C 17/02 (2013.01); H03K 19/018514 (2013.01); H04W 4/80 (2018.02); *A61B 5/1468* (2013.01); *G01N 27/4145* (2013.01)

(58) Field of Classification Search
CPC ........... G01N 27/4148; G01N 27/4145; G06K 7/10376; G06K 19/07749; G08C 17/02
See application file for complete search history.

(56) References Cited

U.S. PATENT DOCUMENTS

| 4,812,785 A * | 3/1989 | Pauker | H03H 11/42 |
| | | | 331/117 FE |
| 8,358,210 B2 | 1/2013 | Goodnow et al. | |
| 8,451,124 B2 | 5/2013 | Lynch et al. | |
| 8,552,730 B2 | 10/2013 | Chiao et al. | |
| 9,295,409 B2 | 3/2016 | Kruglick et al. | |
| 9,544,313 B2 | 1/2017 | Love et al. | |

(Continued)

OTHER PUBLICATIONS

R. A. Gittens, et al., "Electrical Implications of Corrosion for Osseointegration of Titanium Implants", Critical Reviews in Oral Biology & Medicine, Mar. 9, 2011, pp. 1389-1397.

(Continued)

*Primary Examiner* — Nathan W Ha
(74) *Attorney, Agent, or Firm* — Scully, Scott, Murphy & Presser, PC; Erik K. Johnson, Esq.

(57) ABSTRACT

A wireless sensor circuit and sensor tag in which the output is directly converted to a frequency response. The sensor circuit includes a buffer transistor having gate, source and drain terminals configured as a source-follower, a gate resistor connected to the gate terminal of the buffer transistor, a supply voltage connected to the drain terminal of the buffer transistor, and an active load element and a capacitive load element connected to the source terminal of the buffer transistor. An input signal having an input frequency is applied to the buffer transistor via the gate resistor and an output signal is generated at the source terminal of the buffer transistor. The output frequency represents a response of the sensor circuit.

14 Claims, 11 Drawing Sheets

(56) References Cited

U.S. PATENT DOCUMENTS

| | | | |
|---|---|---|---|
| 2010/0301398 A1* | 12/2010 | Rothberg | G01N 27/414 |
| | | | 257/253 |
| 2011/0184264 A1 | 7/2011 | Galasso et al. | |
| 2014/0235452 A1* | 8/2014 | Rothberg | G01N 27/4148 |
| | | | 506/2 |
| 2016/0300240 A1 | 10/2016 | Bright et al. | |
| 2017/0059513 A1 | 3/2017 | Afzali-Ardakani et al. | |
| 2018/0017512 A1 | 1/2018 | Akselrod | |

OTHER PUBLICATIONS

K. Apaza-Bedoya, et al., "Synergistic interactions between corrosion and wear at titanium-based dental implant connections: A scoping review", John Wiley & Sons Ltd, J Periodont Res., Apr. 5, 2017, pp. 946-.

Liao et al., "A 3-μCMOS Glucose Sensor for Wireless Contact-Lens Tear Glucose Monitoring", IEEE Journal of Solid-State Circuits, vol. 47, No. 1, Jan. 2012, pp. 335-344.

D. Pienkowski et al., "The Origin of Stress-Generated Potentials in Fluid-Saturated Bone", Journal of Orthopaedic Research, Raven Press, New York, Jan. 1, 1983, pp. 30-41.

Liu et al., "Ambient Backscatter: Wireless Communication Out of Thin Air", Proceeding SIGCOMM '13 Proceedings of the ACM SIGCOMM 2013 conference on SIGCOMM, Aug. 12-16, 2013, pp. 39-50.

* cited by examiner

CHIPLESS AND WIRELESS SENSOR CIRCUIT AND SENSOR TAG

BACKGROUND OF THE INVENTION

This disclosure is directed to sensor tags and more particularly chipless and wireless sensor circuits.

Sensor tags use RF backscattering systems to enabling wireless charging to eliminate the need for batteries. Wireless sensor tags are advantageous for many wearable and implantable applications, such as for healthcare and structural health/safety monitoring of structures, for example, buildings and bridges. However, prior art sensor tags and sensor tag circuits require a CMOS chip for performing functions such as voltage regulation/bandgap reference, analog-to-digital conversion, current (or voltage) to frequency conversion, pulse generation and frequency modulation. The CMOS chip consumes area, adds weight, reduces mechanical flexibility and increases cost. Even though thin-film transistors capable of operating at RF are available (e.g., low-temperature poly-Si or oxide devices which are much simpler and cheaper than CMOS and compatible with flexible substrates), the CMOS circuits are too complicated to be implemented with non-complementary and lower performance thin-film transistors.

SUMMARY OF THE INVENTION

In one embodiment a wireless sensor circuit is disclosed in which the output is directly converted to a frequency response. In one embodiment, the sensor circuit includes a buffer transistor, having gate, source and drain terminals, that is configured as a source-follower, a gate resistor connected to the gate terminal of the buffer transistor, a supply voltage connected to the drain terminal of the buffer transistor, and an active load element and a capacitive load element connected to the source terminal of the buffer transistor. An input signal having an input frequency is applied to the buffer transistor via the gate resistor and an output signal is generated at the source terminal of the buffer transistor. The output frequency represents a response of the sensor circuit.

In one embodiment of the sensor circuit, the gate resistor is a variable resistor in which the resistance of the gate resistor is a function of a parameter being measured by the sensor circuit. In one embodiment of the sensor circuit, the resistance of the active load or the current sourced by the active load is a function of a parameter being measured by the sensor circuit. In one embodiment of the sensor circuit, the active load is a field-effect transistor with a gate terminal connected to either a source or a drain terminal of the active load field-effect transistor.

In one embodiment a sensor tag is disclosed having a wireless interface, a supply voltage unit and the a sensor circuit in which the supply voltage unit provides a supply voltage to the drain terminal of a transistor of the sensor circuit, the wireless interface provides an input signal to the sensor circuit and the sensor circuit delivers the output signal to the wireless interface. In one embodiment, a sensor tag system is disclosed including one or more sensor tags and an interrogator circuit sending one or more input signals to the wireless interfaces of one or more sensor tags and receiving one or more output signals from the wireless interfaces of one or more sensor tags.

In one embodiment, a method of sensing a stimulus is disclosed including the steps of providing a sensor tag including a wireless interface, a supply voltage unit and a sensor circuit, and exposing the sensor tag to a stimulus thereby generating an output signal at the source terminal of a transistor of the sensor circuit. The output frequency represents a response of the sensor circuit to the stimulus.

Further features as well as the structure and operation of various embodiments are described in detail below with reference to the accompanying drawings. In the drawings, like reference numbers indicate identical or functionally similar elements.

DETAILED DESCRIPTION OF PREFERRED EMBODIMENTS

The present disclosure is directed to a wireless sensor circuit, sensor tag and sensor tag system where the sensor output is directly converted to a frequency response, eliminating the need for voltage regulation/bandgap reference, pulse generation, frequency modulation, and analog-to-digital conversion. The disclosed sensor circuit, tag and system can be implemented with only a few non-complementary transistors, enabling use of transistors with lower performance than CMOS.

Figure 1:
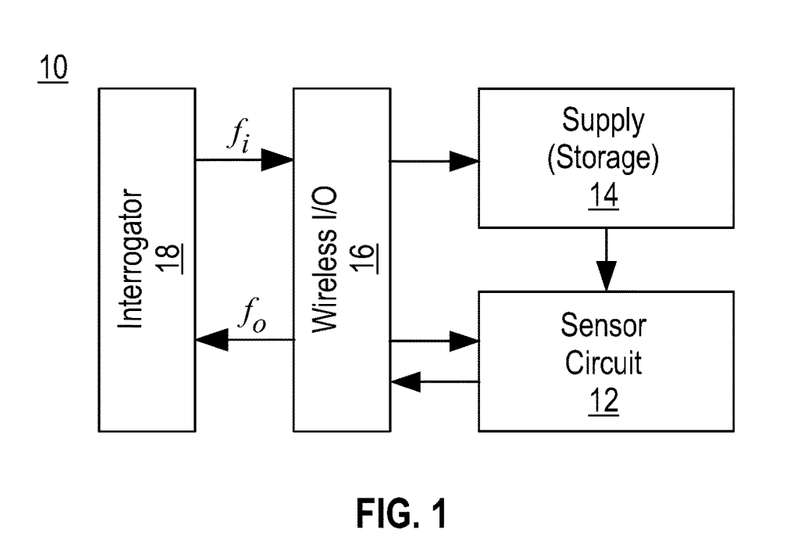
FIG. 1 a block diagram of one embodiment of a sensor tag system disclosed in this specification.

FIG. 1 is a block diagram of one embodiment of a sensor tag system 10 disclosed in this specification. Sensor tag system 10 includes a sensor tag formed of sensor circuit 12, a supply and storage circuit 14 and a wireless input/output (I/O) 16. Sensor tag system 10 includes an interrogator circuit 18. The wireless I/O 16 may include one or more antennas. The antennas may include any antennas known in the art, such as, loop, monopole, dipole, micro-strip, planar, folded, spiral, inverted-F, bowtie and cloverleaf. The supply and storage circuit 14 may include one or more pairs of rectifying diodes and storage capacitors, for example, a Cockcroft Walton voltage multiplier. The supply voltage is preferably supplied wirelessly from Interrogator 18 through wireless I/O 16. However, a battery may be used as a supply voltage.

Figure 2A:
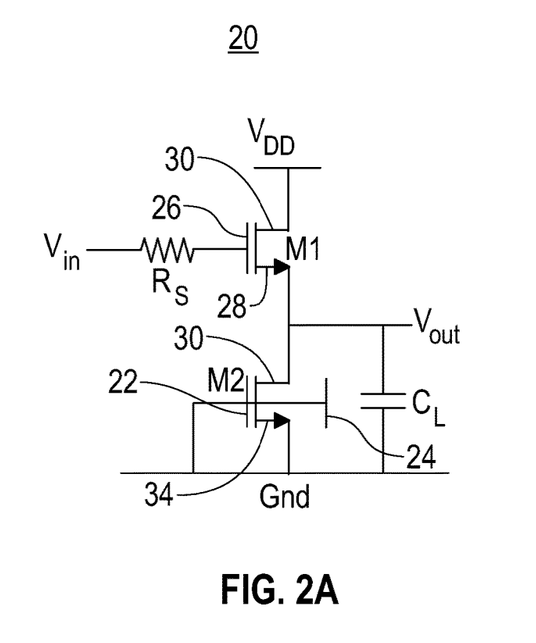
FIG. 2A is a circuit diagram of one embodiment of a sensor circuit disclosed in this specification.

FIG. 2A is a circuit diagram of one embodiment of a sensor circuit 20 of the present disclosure. M1 is an amplifying transistor, and may be a normally-OFF or a normally-ON transistor. M2 is a normally-ON load transistor with its gate connected to its source, and functions as a current source. In preferred embodiments, M1 and M2 are fabricated monolithically and therefore in order to reduce the number of process steps, both are fabricated as normally-ON transistors. M1 and M2 may be depletion-mode MOSFETs or junction field-effect transistors (JFETs), including heterojunction field-effect transistors (HJFETs).

In one embodiment M1 and M2 preferably have threshold voltages close to zero. In one embodiment, M1 and M2 are biased in saturation (either above or below threshold). In one embodiment, M2 is an ion-sensitive field-effect transistor (ISFET) with at least one control gate 22 and one sense gate 24. The sensor circuit 20 includes supply voltage $V_{DD}$, sensor resistance $R_S$, load capacitance $C_L$, input voltage $V_{in}$ and output voltage $V_{out}$.

Figure 2B:
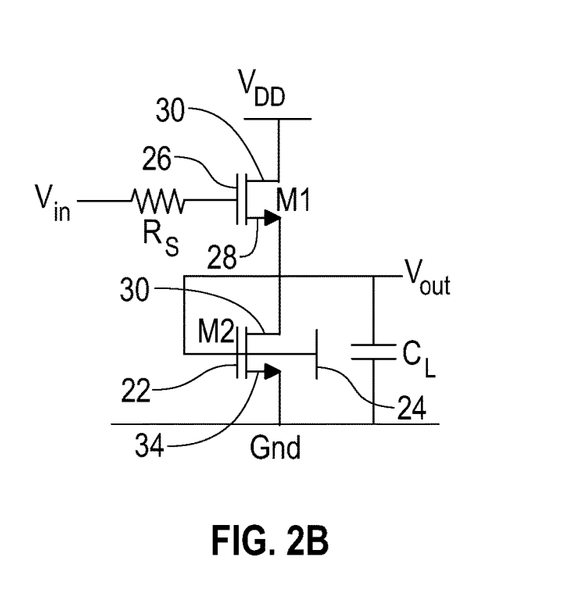
FIG. 2B is a circuit diagram of one embodiment of a sensor circuit disclosed in this specification.

FIG. 2B is a circuit diagram of another embodiment of a sensor circuit 20 of the present disclosure. This circuit diagram is the same as the circuit diagram of FIG. 2A, except that M2 is a normally-OFF load transistor with its gate connected to its drain, and functions as a load resistor, with a resistance value equal to $1/g_{m2}$, where $g_{m2}$ is the transconductance of M2. M1 may be a normally-OFF or a normally-ON transistor; however, in preferred embodiments, M1 and M2 are fabricated monolithically and M1 is also a normally-OFF transistor.

In the sensor circuit 20 of FIG. 2A or 2B, M1 is configured as a source-follower (buffer) transistor having gate terminal 26, source terminal 28 and drain terminal 30. Gate resistor $R_S$ is connected to the gate terminal 26 of buffer transistor M1. Supply voltage $V_{DD}$ is connected to the drain terminal 30 of buffer transistor M1. Active load element, transistor M2 and the capacitive load element $C_L$ are connected to the source terminal 28 of the buffer transistor M1.

The input signal $V_{in}$ having an input frequency is applied to the buffer transistor M1 via the gate resistor $R_S$ and the output signal $V_{out}$ is generated at the source terminal 28 of the buffer transistor M1. The output frequency $f_o$ of the output signal $V_{out}$ represents a response of the sensor circuit 20. The current sourced by the active load element M2 is a function of a parameter being measured by the sensor circuit 20. In one embodiment of sensor circuit 20, the active load is M2 which is a double-gate ISFET, with first gate 24 functioning as a sense gate to measure a parameter being measured by the sensor circuit 20, and second gate 22 connected to drain terminal 30 or source terminal 32 of the active load double-gate ISFET M2. In one embodiment of the sensor circuit 20, the buffer transistor M1 and the active load transistor M2 are biased in saturation.

Figure 3A:
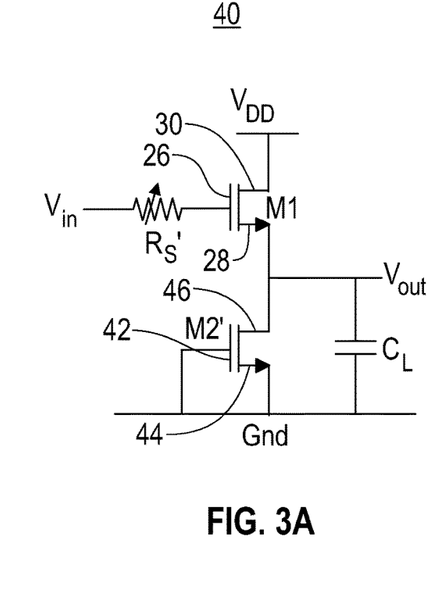
FIG. 3A is a circuit diagram of one embodiment of a sensor circuit disclosed in this specification.

FIG. 3A is a circuit diagram of another embodiment of a sensor circuit 40 disclosed in this specification, in which like elements of FIG. 2A have like reference symbols and numbers. The gate resistor $R_S'$ is a variable resistor that represents the sensor resistance. For example, $R_S'$ may represent a piezo-resistor (strain-gauge) or channel resistance of an ISFET (which may be normally-off or normally-on, with 3 or more terminals). MT is an active-load FET having a gate terminal 42, source terminal 44 connected to GND and a drain terminal 46 connected to source 28 of M1. The gate resistor $R_S'$ is a variable resistor in which the resistance is a function of a parameter being measured by the sensor circuit 40. The output frequency $f_o$ of the output signal $V_{out}$ represents a response of the sensor circuit 40. The active load M2' is a normally-on field-effect transistor with the gate terminal 42 connected to the source terminal 44, and functions as a current source. The buffer transistor may be a normally-OFF or a normally-ON transistor, and preferably a normally-ON transistor in monolithic integrations. In one embodiment, the buffer transistor M1 and the active load transistor M2' are biased in saturation.

Figure 3B:
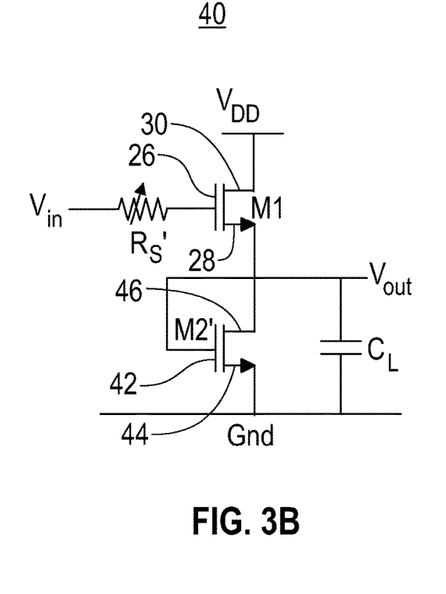
FIG. 3B is a circuit diagram of one embodiment of a sensor circuit disclosed in this specification.

FIG. 3B is a circuit diagram of another embodiment of a sensor circuit 20 of the present disclosure. This circuit diagram is the same as the circuit diagram of FIG. 3A, except that M2 is a normally-OFF load transistor with its gate connected to its drain, and functions as a load resistor, with a resistance value equal to $1/g_{m2}$, where $g_{m2}$ is the transconductance of M2. M1 may be a normally-OFF or a normally-ON transistor; however, in preferred embodiments, M1 and M2 are fabricated monolithically and M1 is also a normally-OFF transistor.

Figure 4A:
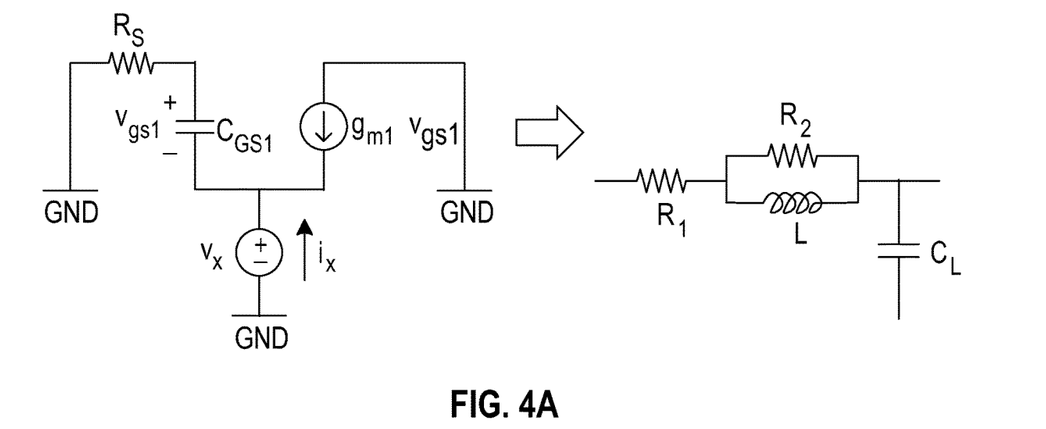
FIG. 4A shows circuit models of one embodiment of a sensor circuit disclosed in this specification.

FIG. 4A is a small-signal model of the sensor circuits of FIGS. 2A and 3A, where $C_{GS1}$ represents the gate-to-source capacitance of M1, and $V_X$ represents the voltage of a test power supply used for determining the output impedance by calculating the current $i_X$ sourced by the test power supply. In the small signal model of FIG. 4A, it is assumed that M1 and M2/M2' are biased in saturation, and therefore the gate-to-drain capacitance values $Cgd_1$ and $Cgd_2$, are small, and the drain-source resistance values $rds_1$ and $rds_2$ are large. Therefore, these parameters are not included in the small signal model. However, as appreciated by those skilled in the art, including these parameters in the small signal model is straightforward.

According to the model circuit of FIG. 4A, the output impedance $Z_{out}$ and output frequency $f_o$ are derived as follows (f denotes ordinary frequency, $\omega=2\pi f$ denotes angular frequency and "||" represents parallel connection):

$$Z_{out} = \frac{v_x}{i_x} = \frac{1 + j\omega R_S C_{GS1}}{g_{m1} + j\omega C_{GS1}} \equiv R_1 + R_2 \| j\omega L \quad \text{Eqn 1}$$

$$= \frac{1}{g_{m1}} + \left(R_S - \frac{1}{g_{m1}}\right) \left\| \left[\frac{j\omega C_{GS1}}{g_{m1}}\left(R_S - \frac{1}{g_{m1}}\right)\right]\right.$$

$$\Rightarrow f_o = 1/2\pi \sqrt{\frac{C_{GS1} C_L}{g_{m1}}\left(R_S - \frac{1}{g_{m1}}\right)} \quad \text{Eqn 2}$$

Eqn 1 indicates that the small signal model can be represented by an equivalent circuit with a first equivalent resistor $R_1=1/g_{m1}$, a second equivalent resistor $R_2=R_S-1/g_{m1}$ and an equivalent inductor $L=(C_{GS1}/g_{m1})\cdot(R_S-1/g_{m1})$, as illustrated in FIG. 4A, where L creates resonance with the load capacitor $C_L$ at output frequency $f_o$ given by Eqn 2, and the equivalent resistors have a damping effect on oscillation at resonance. Therefore larger $g_{m1}$ results in lower damping. With respect to circuit 20 shown in FIG. 2A, $g_{m1}$ is a function of the current sourced by M2, $I_{D2}$ (typically $g_{m1}$ is proportional to $I_{D1}^{1/2}$, and $I_{D1}=I_{D2}$, therefore $g_{m1}$ is proportional to $I_{D2}^{1/2}$) and $I_{D2}$ in turn is a function of the stimulus being sensed. Therefore, $f_o$ is also a function of the stimulus as evident from Eqn 2. With respect to circuit 40 shown in FIG. 3A, $R_S'$ is a function of the stimulus being sensed. Therefore, $f_o$ is also a function of the stimulus as evident from Eqn 2.

Figure 4B:
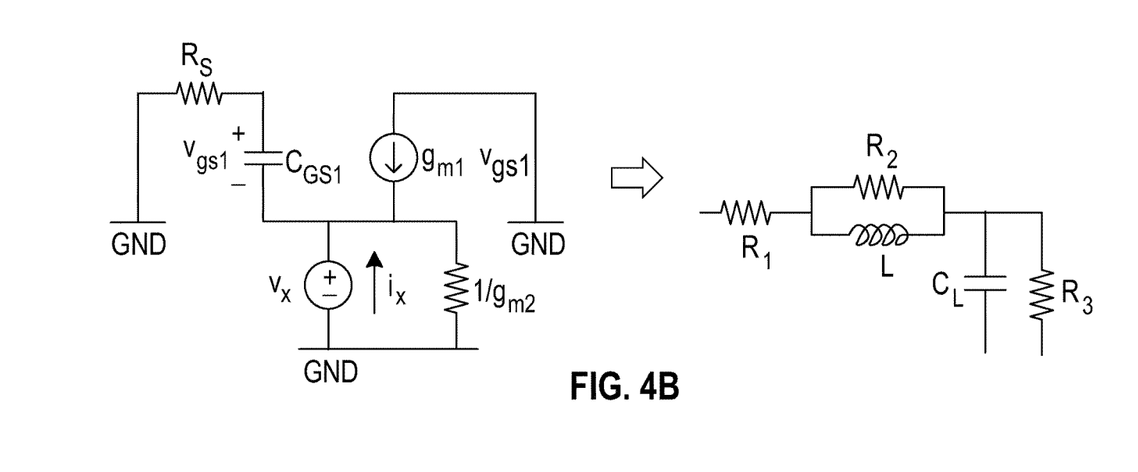
FIG. 4B shows circuit models of another embodiment of a sensor circuit disclosed in this specification.

FIG. 4B is a small-signal model of the sensor circuits of FIGS. 2B and 3B. The equivalent circuit is the same as that derived in FIG. 4A, with the addition of a third equivalent resistor $R_3=1/g_{m2}$ in parallel with $C_L$. Given that the parallel combination of $R_3$ and $C_L$ creates a pole at frequency $\frac{1}{2\pi(R_3 C_L)}$, $R_3$ must be chosen large to avoid limiting the operation frequency. For example, a small $(W/L)_2$ may be used for M2 to obtain a small $g_{m2}$, whereas a large $(W/L)_1$ may be used for M1 to obtain a large $g_{m1}$, where W/L refers to the channel width-to-length ratio.

Figure 4C:
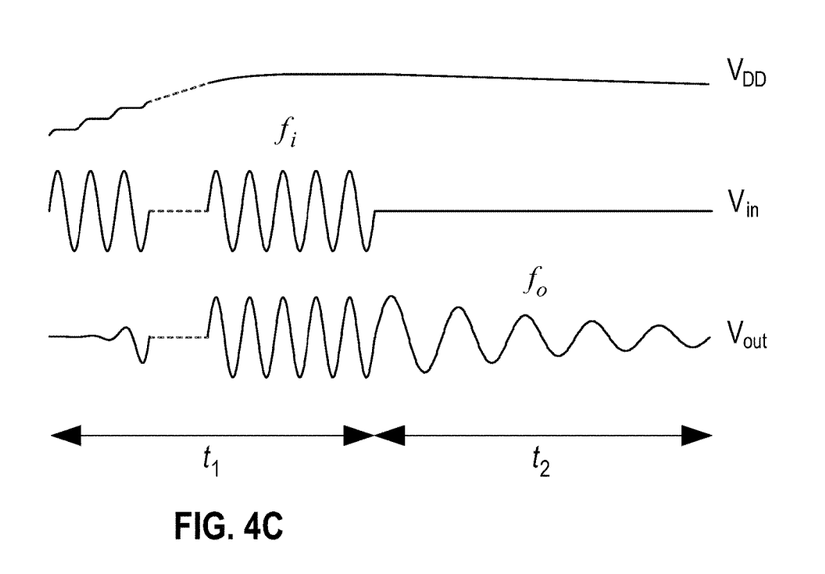
FIG. 4C is an illustration of an example of an operation of a sensor circuit in one or more embodiments of this specification.

An example of an operation of the sensor circuit 20 or 40 (corresponding to sensor circuit 12 shown in FIG. 1) and a schematic illustration of the input ($V_{in}$), output ($V_{out}$) and the supply voltage ($V_{DD}$) as a function of time is shown in FIG. 4C and is applicable to one or more embodiments. The sensor circuit 20 shown in FIG. 2A is used for illustration, but the exemplary operation described with respect to FIG. 4C is applicable to the sensor circuits shown in FIGS. 2B, 3A and 3B as well. A rectifier circuit is connected between $V_{in}$ and $V_{out}$. The rectifier circuit may be, e.g. a single diode-capacitor pair or a Cockroft-Walton multiplier. The rectifier circuit corresponds to the supply (storage) unit 14 shown in FIG. 1. In operation, an input signal $V_{in}$ having an input frequency $f_i$ simultaneously charges $V_{DD}$ and excites the sensor circuit, during a time period $t_1$. During this period, the output $V_{out}$ oscillates with the same frequency $f_i$. Thereafter, the input signal is turned off and during a following time period $t_2$ the sensor circuit oscillates at $f_o$ derived above (Eqn 2). Even though $V_{DD}$ may partially discharge during time period $t_2$, it does not need regulation so far as it remains large enough to ensure M1 and M2 are in saturation. It will be appreciated that the sensor circuit may contain, or operate in conjunction with additional components not shown in the figure and the waveforms shown for $V_{in}$, $V_{out}$ and $V_{DD}$ are illustrative.

Figure 5A:
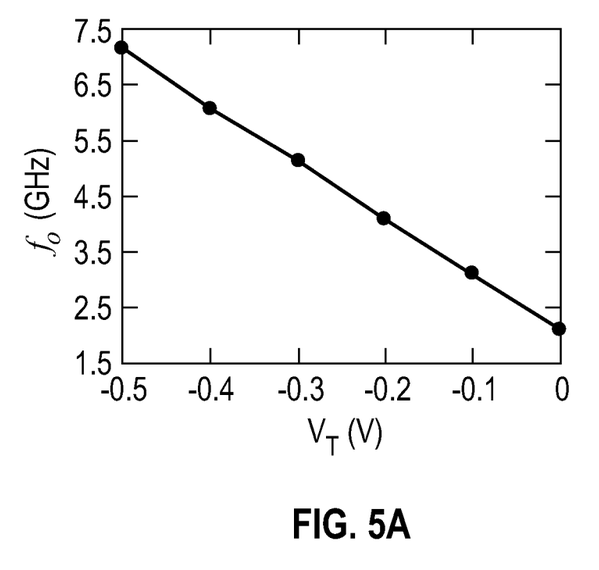
FIG. 5A is a graph of a simulation of the sensor circuit of FIG. 2A.
Figure 5B:
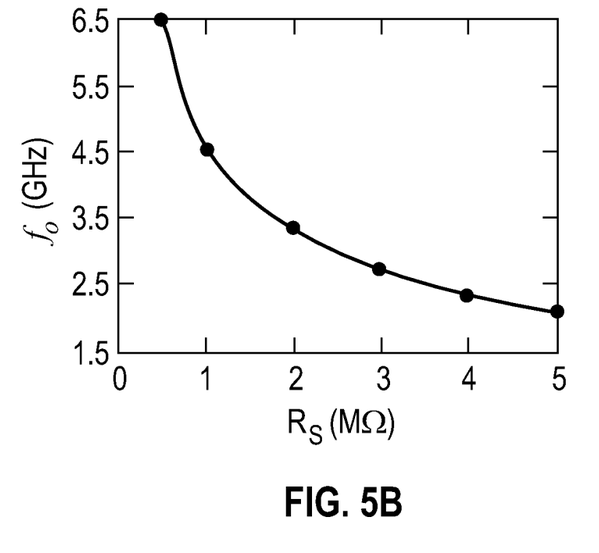
FIG. 5B is a graph of a simulation of the sensor circuit of FIG. 3A.

FIG. 5A is a graph of a simulation of an example of the sensor circuit of FIG. 2A. In this simulation, $R_S=5M\Omega$, $g_{m1}=3$ mA/V, $C_{GS1}=1$ fF, $C_L=2$ fF, $f_i=5$ GHz and $V_T$, the threshold voltage of M2, is varied as a function of the simulus applied to the sense gate of M2. Since the current $I_{D2}$ sourced by M2 is a function of $V_T$, therefore $g_{m1}$ and $f_o$ vary by the application of the simulus, as described by Eqn 2. In this example, if M2 is a PH sensor with sensitivity of 50 mV/PH (~17% lower than the Nernst Limit of 60 mV/PH), the simulated $V_T$ range −0.5-0.0V corresponds to a PH range of 10 (i.e. 500 mV/10 PH). FIG. 5B is a graph of a simulation of an example of the sensor circuit of FIG. 3A. In this simulation, $g_{m1}=3$ mA/V, $C_{GS1}=1$ fF, $C_L=2$ fF, $f_i=5$ GHz, $V_T=0$V and $R_S$ is variable as a function of the stimulus applied to $R_S$. As described by Eqn 2, $f_o$ varies by varying $R_S$.

Figure 5C:
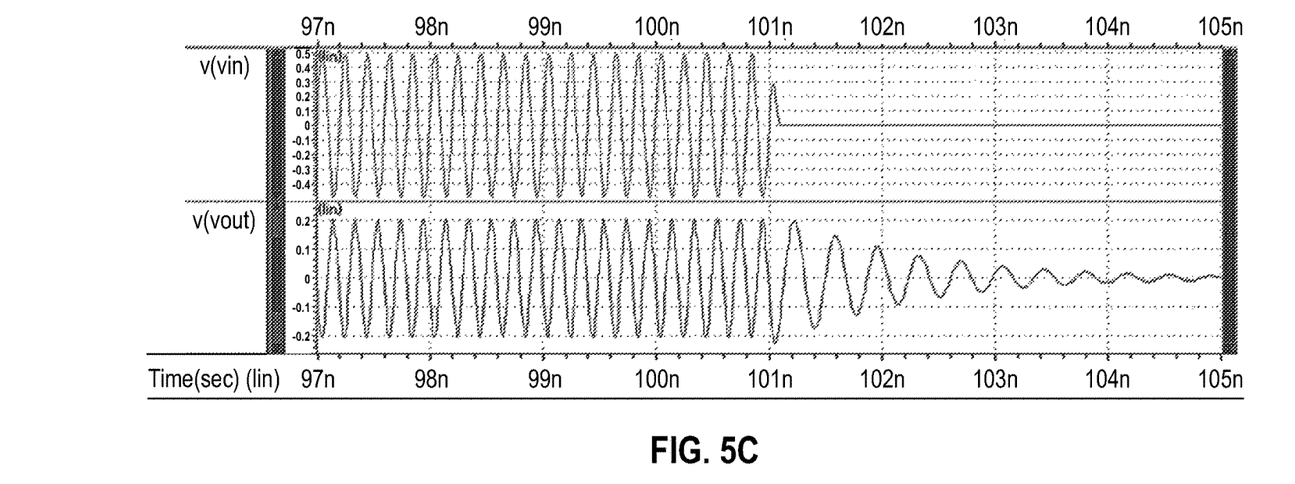
FIG. 5C is a graph of a simulation of the sensor circuit of FIG. 2A.

FIG. 5C is a graph of a simulation of an example of the sensor of FIG. 2A. In this simulation, $R_S=3M\Omega$, $V_T=0$V, $g_{m1}=3$ mA/V, $C_{GS1}=1$ fF, $C_L=2$ fF and $f_i$ 5 GHz. Until about t=101 ns, the output oscillates at the same frequency as the input (5 GHz). At about t=101 ns, the input ($v_{in}$) is switched off, and thereafter the output oscillates at $f_o \approx 3$ GHz.

Figure 5D:
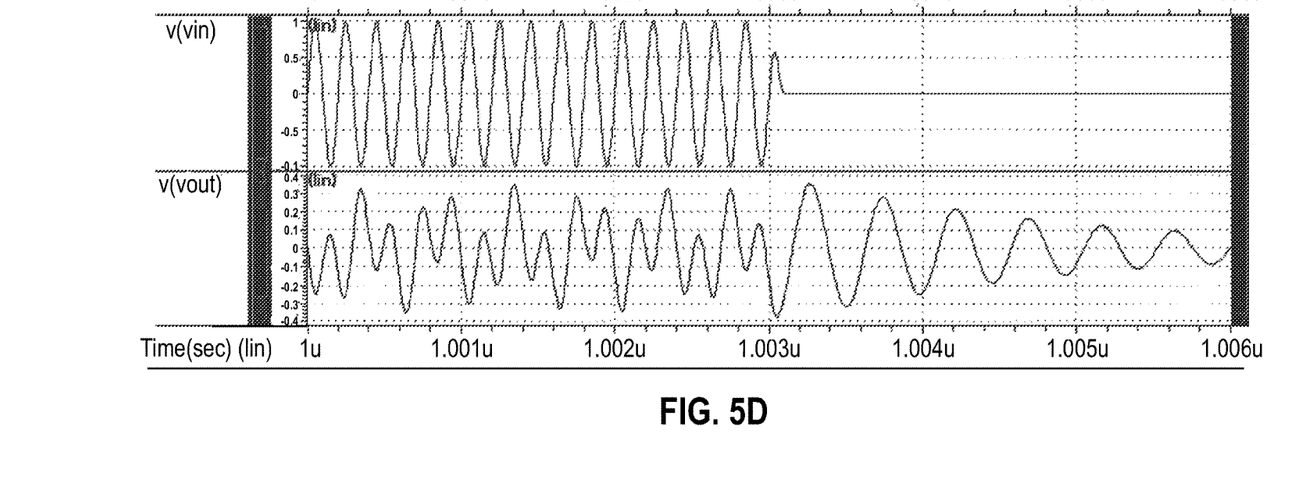
FIG. 5D is a graph of another simulation of the sensor circuit of FIG. 2A.
Figure 5E:
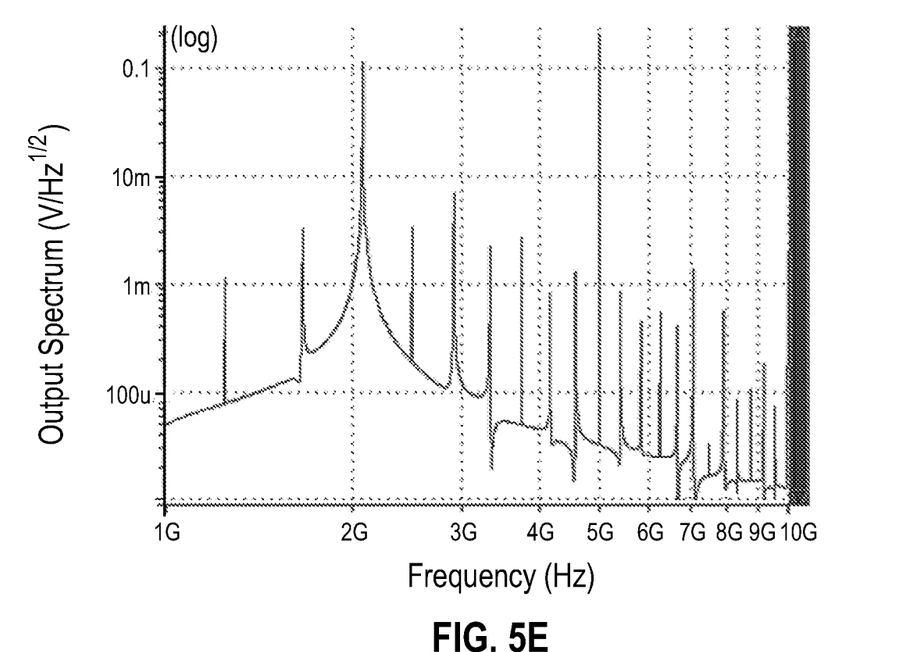
FIG. 5E is a graph of the calculated frequency spectrum of a portion of the simulation graph of FIG. 5D.

In some embodiments, depending on the input and output frequencies and input amplitude, the output signal during charging may contain both the input and the output frequencies. Therefore, the backscattering signal during charging may also be used by the interrogator for reading. In these embodiments, preferably the output is isolated from the input during charging and/or separate antennas are used for receiving the input and transmitting the output. FIG. 5D is a graph of a simulation of another example of the sensor of FIG. 2A, with $R_S=5M\Omega$, $V_T=0$V, $C_L=2$ fF, $g_{m1}=3$ mA/V, $C_{GS1}=1$ fF and $f_i=5$ GHz. The simulated output frequency $f_o \approx 2$ GHz. Until about t=1.003 μs, the output oscillation includes both $f_i$ and $f_o$. This is evident from the frequency spectrum of the output shown in FIG. 5E, which has two peaks at 5.0 GHz and 2.1 GHz. The frequency spectrum was obtained by calculating the Fourier transform of the output voltage, $V_{out}$, from t=0.5 μs to t=1 μs. At about t=1.003 μs, the input is switched off, and thereafter the output oscillation only contains $f_o$.

Figure 6:
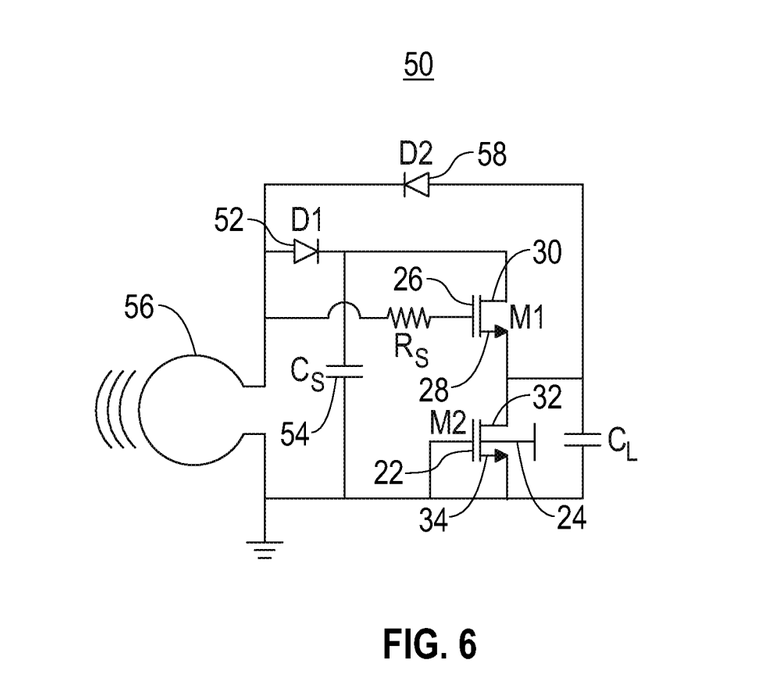
FIG. 6 is a circuit diagram of another embodiment of a sensor circuit disclosed in this specification.

FIG. 6 is one embodiment of a sensor tag 50 with the sensor circuit of FIG. 2A, having a single-stage rectifier diode D1, 52 and storage capacitor $C_S$, 54. Increasing the storage capacitance value reduces the voltage drop after charging (by storing more charge) but also increases the time required for charging. Sensor tag 50 also includes a loop antenna 56. The antennas shown in the sensor tags described in this embodiment and other embodiments below are not limited to loop antennas. In one embodiment, the wireless interface includes a receiving antenna for receiving an input signal and a transmitting antenna for transmitting the output signal. In one embodiment, the receiving antenna and the sending antenna have different polarizations. In one embodiment, the receiving antenna and the sending antenna are linearly polarized perpendicular to each other. A diode may be, for example, a p-n junction diode, a p-i-n diode, a Schottky diode or a diode-connected transistor.

In one embodiment the sensor tag 50, a separate antenna connected across $C_L$ (not shown) may be used for sending the output signal signals. In one embodiment, the sending and receiving antennas may be configured concentrically to save space.

Sensor tag 50 may include optional diode D2, 58 connected to isolate the output from antenna 56 during $V_{DD}$ charging. The additional diode 58 may be beneficial for reducing power consumption during charging and interference in some embodiments.

Figure 7:
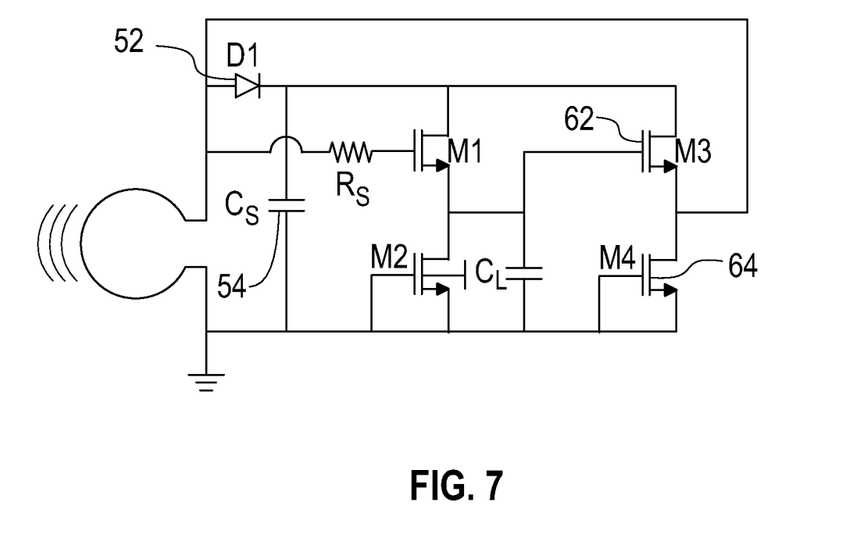
FIG. 7 is a circuit diagram of another embodiment of a sensor circuit disclosed in this specification.

FIG. 7 is one embodiment of a sensor tag 60 with the sensor circuit of FIG. 2A having single-stage rectifier diode D1, 52 and capacitor $C_S$, 54 and a buffer stage formed by transistors M3, 62 and M4, 64. The buffer stage may be beneficial for impedance matching in some embodiments.

Figure 8:
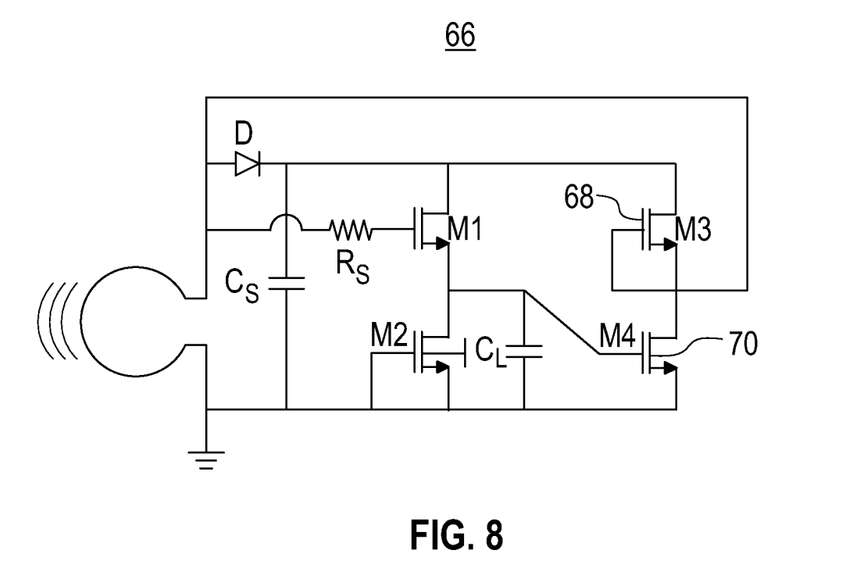
FIG. 8 is a circuit diagram of another embodiment of a sensor circuit disclosed in this specification.

FIG. 8 is one embodiment of a sensor tag 66 with an output amplifier stage formed of transistor M3, 68, M3 and transistor M4, 70.

Figure 9:
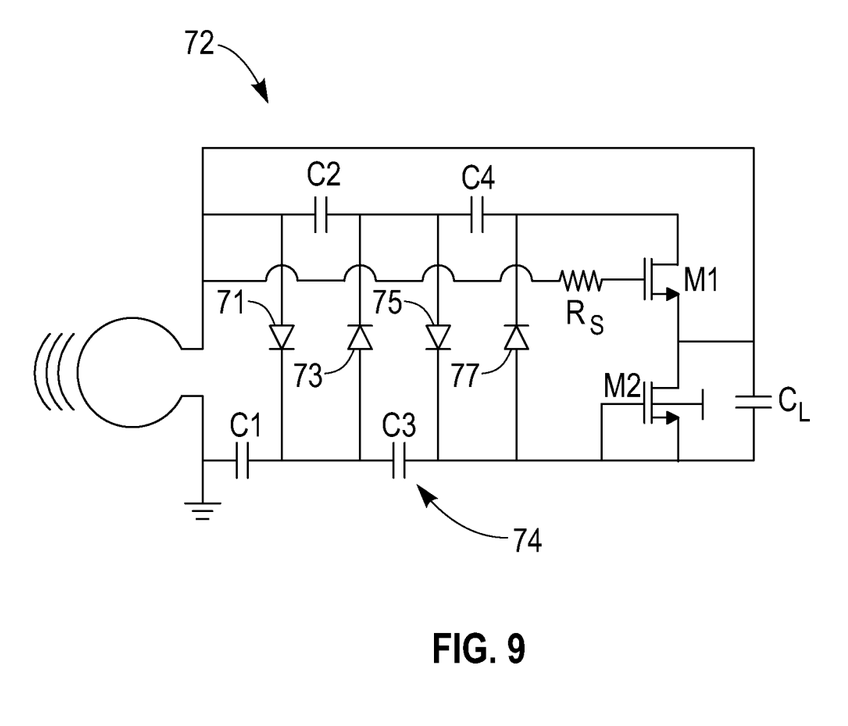
FIG. 9 is a circuit diagram of another embodiment of a sensor circuit disclosed in this specification.
Figure 10:
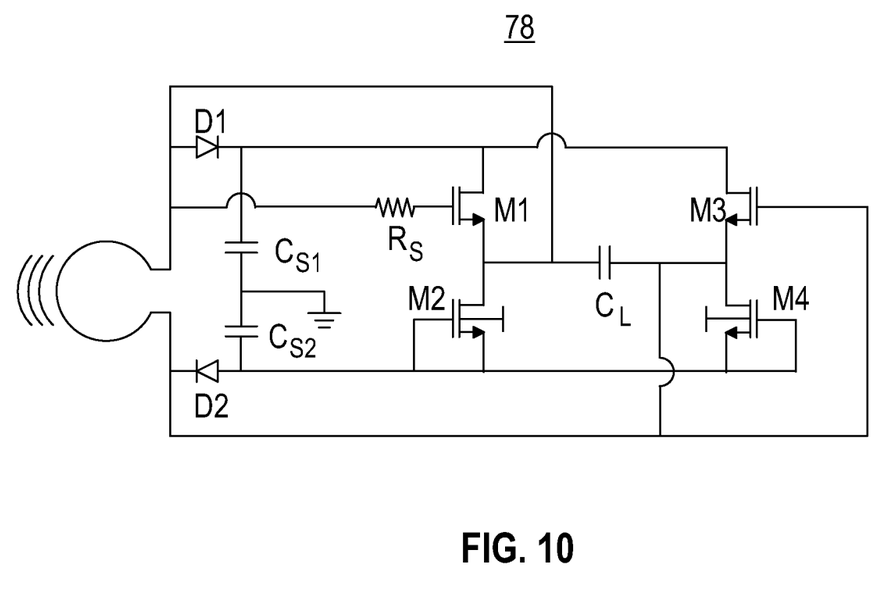
FIG. 10 is a circuit diagram of another embodiment of a sensor circuit disclosed in this specification.
Figure 11:
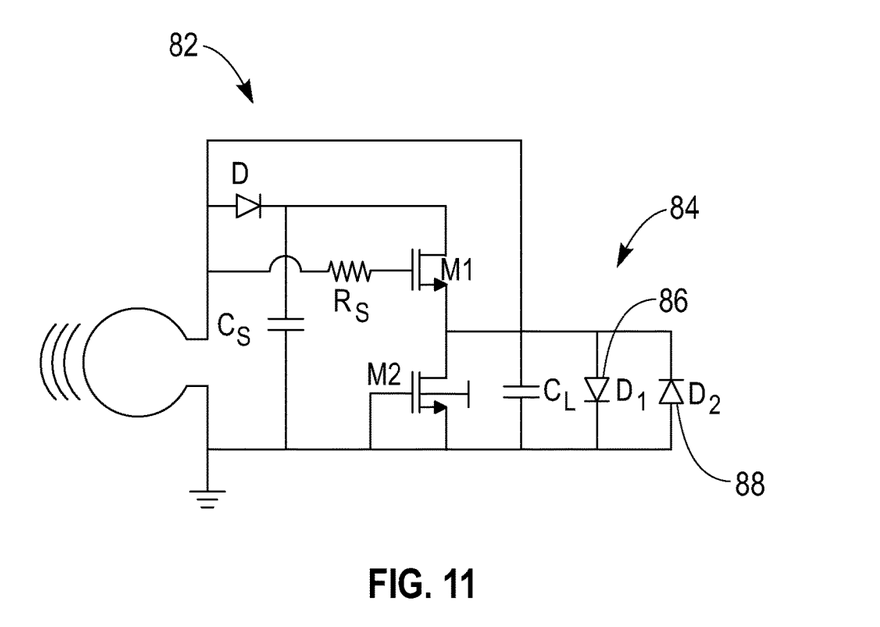
FIG. 11 is a circuit diagram of another embodiment of a sensor circuit disclosed in this specification.

FIG. 9 is one embodiment of a sensor tag 72 with a 4-stage Cockroft Walton rectifier 74 (voltage doubler) formed by capacitors C1-C4 and diodes 71, 73, 75, 77. FIG. 10 is one embodiment of a sensor tag 78 with a differential circuit instead of single-ended design formed of rectifier diodes D1 and D2, storage capacitors $C_{S1}$ and $C_{S2}$ and output transistors M3 and M4. FIG. 11 is one embodiment of a sensor tag 82 with a clamping stage 84 formed of diode D1, 86 and diode D2, 88 at the output.

In one embodiment, perpendicular linear polarizations for the input and output antennas may be used to minimize interference. In one embodiment, a sensor tag and a reference tag with perpendicular linear polarizations may be used for independent communication with minimal interference.

In one exemplary embodiment, a sensor tag may be used for monitoring a medical implant, such as a dental implant, for deterioration or corrosion. Medical implants may fail for various reasons, including indirect physiological reasons or corrosion, leading to problems such as chronic pain, tissue damage, bone resorption, inflammation, fibrosis, loosening of implant, and infection.

In one example, a sensor tag having a sensor circuit of FIG. 6 in which M2 is an ISFET, with extended gate 24, functionalized for PH measurement. The sensor tag is placed on the implanted tooth and a reference sensor tag is placed on a healthy natural tooth. The sensor tag may be used for monitoring for corrosion by measuring PH in surrounding bodily fluids, e.g. saliva around an implanted tooth. Data may be collected on an ambulatory basis, periodically or initiated by the patient at the onset of symptoms, or at appropriate times, e.g., immediately after waking up.

In another exemplary embodiment, a sensor tag may be used for monitoring of bone health. The differential voltage generated on bones under mechanical strain may be monitored, for example, during recovery from fracture or in the course of a therapeutic procedure, such as in orthodontics or when a metal implant generates strain in surrounding bone. A sensor tag as shown in FIG. 10 may be used in which M2 and M4 are double-gate transistors, with one gate (which may be an extended gate) in electrical contact with bone. As known in the art, the voltage sensed by one gate of a double-gate transistor changes the threshold voltage of the double-gate transistor. Therefore, direct sensing of voltage (or voltage difference in differential circuits) is applicable in the same manner as described with respect to FIG. 5A, with voltage (e.g. surface voltage of bone) being the stimulus.

In another exemplary embodiment, a sensor tag may be used for monitoring structural health, such as of bridges. In this example, the interrogator is carried by a petrol vehicle. Sensor tags as shown in FIG. 3A are installed at various locations on the bridge. The sensor tags with piezo-resistive sensor elements ($R_S'$) shown in FIG. 3A are used for monitoring the structural health of the bridges and to identify locations that potentially need repair. Application to other structures, e.g. buildings, towers, is also be contemplated. Given that antenna size can be large in this application, the operation frequency and therefore transistor performance can be low accordingly, allowing low tag cost and mass deployment.

In one exemplary embodiment, a sensor tag may be used as a wearable chemical/biological sensor, such as a glucose sensor. In one example, the sensor tag of FIG. 6 is used in which M2 is a double-gate ISFET with one gate, e.g., back-gate 22 is connected to source 34 of M2 and one gate, e.g., front-gate 24 (which may be an extended gate) is functionalized to measure chemical and/or biological species. The double-gate ISFET may be a JFET-based glucose sensor. However, various other double-gate ISFET structures known in the art may be used as well.

The ISFET devices are not limited to glucose sensors. The sense gate of the ISFET may be functionalized using techniques known in the art to sense various species.

When used as a glucose sensor, the sensor tag may be placed on an eye lens or may be used to sense glucose in other body fluids, e.g., saliva or sweat, as known in the art.

In one embodiment of the sensor tag of FIG. 6 used as a wearable chemical/biological sensor, the gate resistor $R_S$ is replaced by a transistor $M_S$ which is a single-gate ISFET (e.g., an extended gate FET). $M_S$ may also be a JFET (including an HJFET) device, where $R_S=2 L/[\mu_b C_D W(V_{GS}-V_P)]$, where W is the channel width, L is the channel length, $C_D$ is the gate depletion capacitance per unit area and $V_P$ is the pinch-off voltage of the JFET or HJFET. $M_S$ may also be an MOS device, where $R_S=L/[\mu_{FE} C_i W(V_{GS}-V_T)]$, where $C_i$ is the gate dielectric capacitance per unit area of the MOS transistor. In these embodiments, $V_T$ or $V_P$ vary as a function of the species being sensed.

Figure 12A:
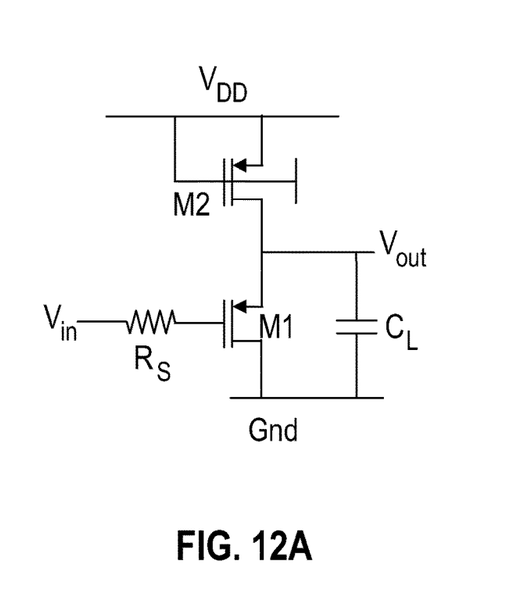
FIG. 12A is a circuit diagram of an embodiment of a sensor circuit disclosed in this specification.
Figure 12B:
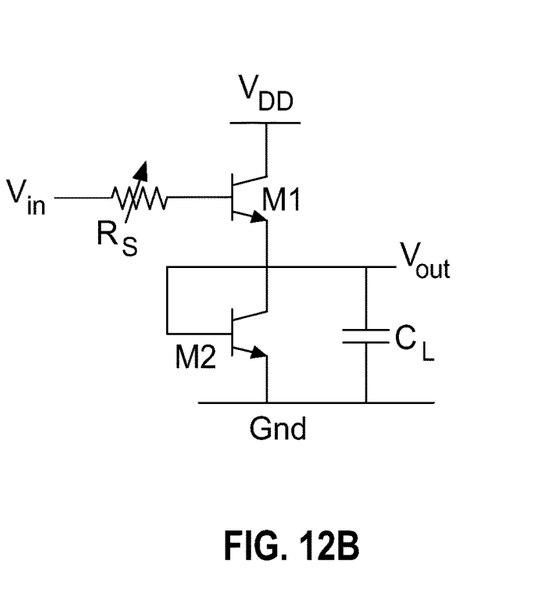
FIG. 12B is a circuit diagram of a sensor circuit disclosed in this specification.

While the circuit diagrams discussed with respect to FIGS. 2 through 11 are implemented with n-channel transistors, it will be appreciated by those skilled in the art that these circuits may also be implemented with p-channel transistors with necessary adjustments to account for the opposite voltage polarities needed for p-channel transistors. Also, it will be appreciated that bipolar junction transistors (including heterojunction bipolar transistors) may also be used in some embodiments. For example, FIG. 12A is an implementation of the circuit of FIG. 2A using p-channel transistors, and FIG. 12B is an implementation of the circuit of FIG. 3B using n-p-n bipolar junction transistors.

Figure 13:
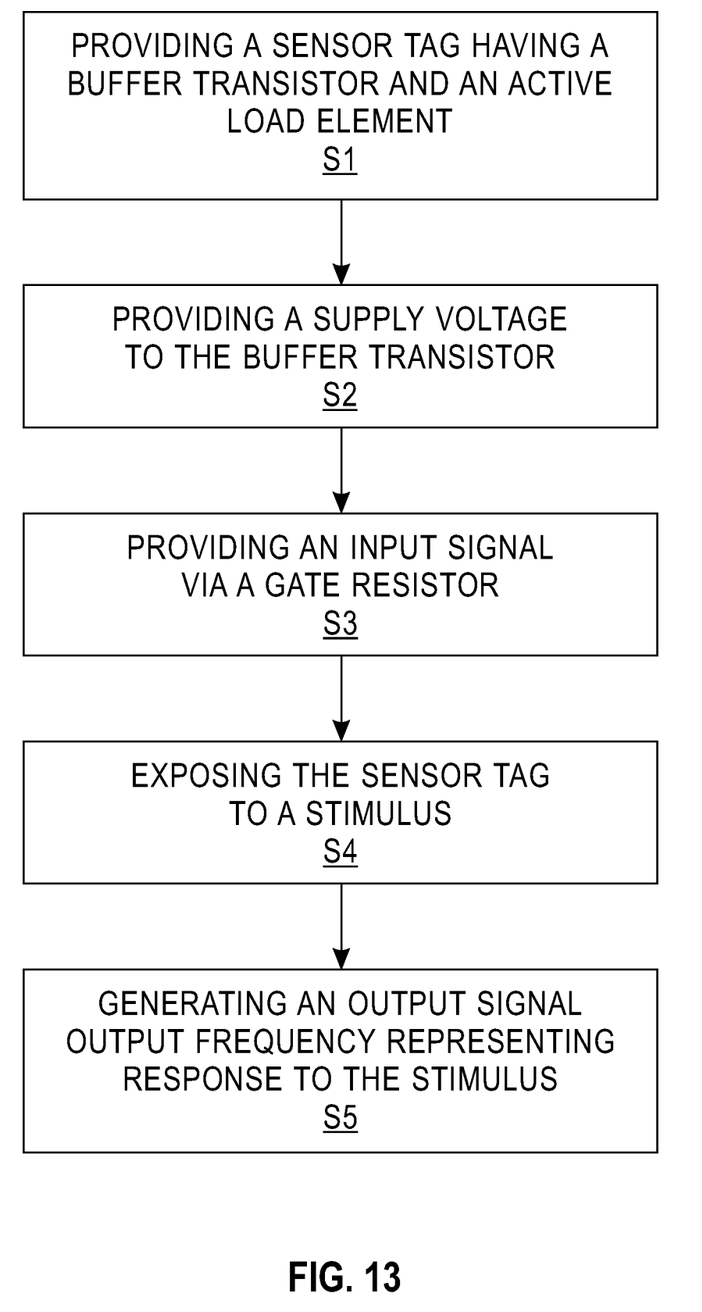
FIG. 13 is flow diagram of one embodiment of a method of sensing a stimulus using one embodiment of a sensor circuit disclosed in this specification.

FIG. 13 is a flow diagram of one embodiment of a method of sensing a stimulus. The method includes step S1 of providing a sensor tag. The sensor tag includes a wireless interface, a supply voltage source and a sensor circuit. The sensor circuit includes a buffer transistor configured as a source-follower, the buffer transistor having gate, source and drain terminals, a gate resistor connected to the gate terminal of the buffer transistor and an active load element and a capacitive load element connected to the source terminal of the buffer transistor.

The method includes step S2 of providing a supply voltage connected to the drain terminal of the buffer transistor and step S3 of providing an input signal having an input frequency applied to the buffer transistor via the gate resistor. The method includes step S4 of exposing the sensor tag to a stimulus and step S5 of generating an output signal in which the output frequency represents a response of the sensor circuit to the stimulus.

Figure 14:
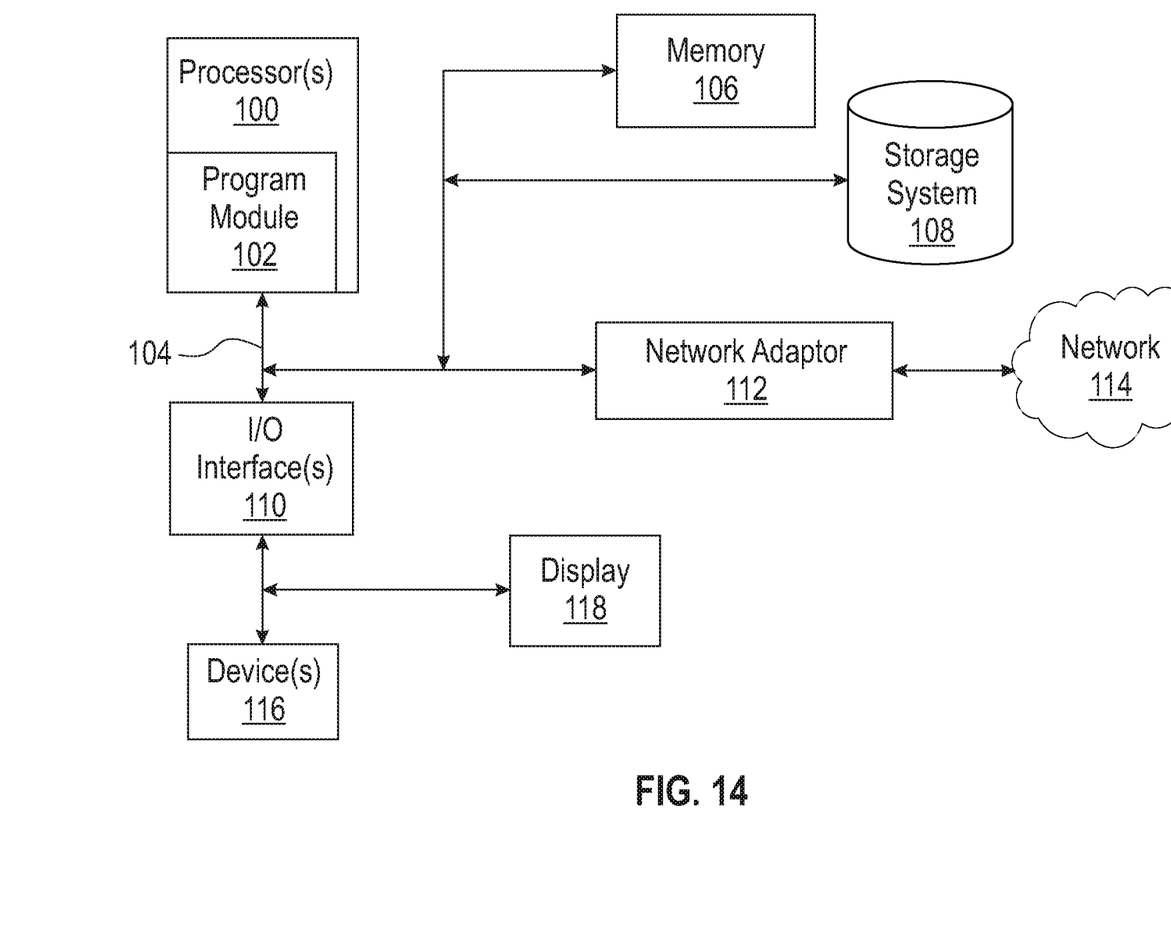
FIG. 14 is a block diagram of an exemplary computing system suitable for implementation of the embodiments of the invention disclosed in this specification.

FIG. 14 illustrates a schematic of an example computer or processing system that may implement the interrogator of FIG. 1 in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 14 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 100, a system memory 106, and a bus 104 that couples various system components including system memory 106 to processor 100. The processor 100 may include a program module 102 that performs the methods described herein. The module 102 may be programmed into the integrated circuits of the processor 100, or loaded from memory 106, storage device 108, or network 114 or combinations thereof.

Bus 104 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 106 can include computer system readable media in the form of volatile memory, such as random access memory (RAM) and/or cache memory or others. Computer system may further include other removable/non-removable, volatile/non-volatile computer system storage media. By way of example only, storage system 108 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 104 by one or more data media interfaces.

Computer system may also communicate with one or more external devices 116 such as a keyboard, a pointing device, a display 118, etc.; one or more devices that enable a user to interact with computer system; and/or any devices (e.g., network card, modem, etc.) that enable computer system to communicate with one or more other computing devices. Such communication can occur via Input/Output (I/O) interfaces 110.

Still yet, computer system can communicate with one or more networks 114 such as a local area network (LAN), a general wide area network (WAN), and/or a public network (e.g., the Internet) via network adapter 112. As depicted, network adapter 112 communicates with the other components of computer system via bus 104. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a non-transitory computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

In addition, while preferred embodiments of the present invention have been described using specific terms, such description is for illustrative purposes only, and it is to be understood that changes and variations may be made without departing from the spirit or scope of the following claims.

What is claimed is:

1. A sensor circuit, comprising:
   a buffer transistor configured as a source-follower, the buffer transistor having gate, source and drain terminals;
   a gate resistor connected to the gate terminal of the buffer transistor;
   a supply voltage connected to the drain terminal of the buffer transistor;
   an active load element comprising a transistor having a drain terminal connected to the source terminal of the buffer transistor, a control gate terminal connected to ground, a source terminal connected to ground and a sense gate terminal;
   a capacitive load element connected between the source terminal of the buffer transistor and ground;
   an input signal having an input frequency applied to the buffer transistor via the gate resistor; and
   an output signal generated at the source terminal of the buffer transistor, the output signal having an output frequency;
   wherein the output frequency represents a response of the sensor circuit.

2. The sensor circuit of claim 1, wherein the gate resistor is a variable resistor in which the resistance of the gate resistor is a function of a parameter being measured by the sensor circuit.

3. The sensor circuit of claim 1, wherein the resistance of the active load or the current sourced by the active load is a function of a parameter being measured by the sensor circuit.

4. The sensor circuit of claim 1, wherein the active load element is a normally-on field-effect transistor.

5. The sensor circuit of claim 1, wherein the buffer transistor is biased in saturation.

6. The sensor circuit of claim 1, wherein the active load element is an ion-sensitive field-effect transistor (ISFET).

7. The sensor circuit of claim 6, wherein the active load element is a double-gate ISFET, with the sense gate configured to measure a parameter being measured by the sensor circuit.

8. A sensor circuit, comprising:
- a buffer transistor configured as a source-follower, the buffer transistor having gate, source and drain terminals;
- a gate resistor connected to the gate terminal of the buffer transistor;
- a supply voltage connected to the drain terminal of the buffer transistor;
- an active load element comprising a transistor having a drain terminal connected to the source terminal of the buffer transistor, a control gate terminal connected to the source terminal of the buffer transistor, a source terminal connected to ground and a sense gate terminal;
- a capacitive load element connected between the source terminal of the buffer transistor and ground;
- an input signal having an input frequency applied to the buffer transistor via the gate resistor; and
- an output signal generated at the source terminal of the buffer transistor, the output signal having an output frequency;

wherein the output frequency represents a response of the sensor circuit.

9. The sensor circuit of claim 8, wherein the gate resistor is a variable resistor in which the resistance of the gate resistor is a function of a parameter being measured by the sensor circuit.

10. The sensor circuit of claim 8, wherein the resistance of the active load or the current sourced by the active load is a function of a parameter being measured by the sensor circuit.

11. The sensor circuit of claim 8, wherein the active load element is a normally-off field-effect transistor.

12. The sensor circuit of claim 8, wherein the buffer transistor is biased in saturation.

13. The sensor circuit of claim 8, wherein the active load element is an ion-sensitive field-effect transistor (ISFET).

14. The sensor circuit of claim 13, wherein the active load element is a double-gate ISFET, with the sense gate configured to measure a parameter being measured by the sensor circuit.

* * * * *